(12) United States Patent
Laico

(10) Patent No.: US 9,186,377 B2
(45) Date of Patent: Nov. 17, 2015

(54) METHOD, COMPOSITION, AND ARTICLES FOR IMPROVING JOINT LUBRICATION

(75) Inventor: Joseph P. Laico, New City, NY (US)

(73) Assignee: Maguire Abbey, LLC, Wilmington, DE (US)

( * ) Notice: Subject to any disclaimer, the term of this patent is extended or adjusted under 35 U.S.C. 154(b) by 0 days.

(21) Appl. No.: 13/487,470

(22) Filed: Jun. 4, 2012

(65) Prior Publication Data

US 2012/0308510 A1    Dec. 6, 2012

Related U.S. Application Data

(60) Provisional application No. 61/493,124, filed on Jun. 3, 2011.

(51) Int. Cl.
| | | |
|---|---|---|
| A61K 31/765 | (2006.01) | |
| C08G 63/08 | (2006.01) | |
| A61P 19/02 | (2006.01) | |
| A61L 27/58 | (2006.01) | |
| A61L 27/50 | (2006.01) | |
| A61F 2/30 | (2006.01) | |

(52) U.S. Cl.
CPC ............ *A61K 31/765* (2013.01); *A61L 27/50* (2013.01); *A61L 27/58* (2013.01); *A61F 2002/30673* (2013.01); *A61L 2430/24* (2013.01); *Y10T 428/2982* (2015.01)

(58) Field of Classification Search
CPC .. A61K 31/765; A61K 2300/00; A61K 45/06
USPC ........................................ 424/78.38; 428/402
See application file for complete search history.

(56) References Cited

U.S. PATENT DOCUMENTS

| | | | | |
|---|---|---|---|---|
| 4,713,446 | A * | 12/1987 | DeVore et al. ................. | 530/356 |
| 6,126,690 | A | 10/2000 | Ateshian et al. | |
| 6,383,228 | B1 | 5/2002 | Schmotzer et al. | |
| 6,960,562 | B2 * | 11/2005 | Jay ............................... | 514/20.9 |
| 7,550,573 | B2 | 6/2009 | Goddard et al. | |
| 2003/0203030 | A1 | 10/2003 | Ashton et al. | |
| 2005/0004073 | A1 | 1/2005 | Gislason et al. | |
| 2005/0043808 | A1 * | 2/2005 | Felt et al. .................... | 623/20.14 |
| 2005/0152949 | A1 | 7/2005 | Hotchkiss et al. | |
| 2006/0106011 | A1 | 5/2006 | Bock et al. | |
| 2007/0071840 | A1 * | 3/2007 | Dhanaraj et al. .............. | 424/764 |
| 2007/0141160 | A1 | 6/2007 | Brown et al. | |
| 2007/0142480 | A1 | 6/2007 | Niazi | |
| 2007/0160594 | A1 | 7/2007 | Filvaroff et al. | |
| 2007/0167397 | A1 | 7/2007 | Dillon et al. | |
| 2008/0097606 | A1 | 4/2008 | Cragg et al. | |
| 2009/0005869 | A1 | 1/2009 | Laurencin et al. | |
| 2009/0017096 | A1 | 1/2009 | Lowman et al. | |
| 2009/0111763 | A1 | 4/2009 | Fritz et al. | |
| 2009/0208589 | A1 | 8/2009 | Grinstaff et al. | |
| 2009/0246123 | A1 | 10/2009 | Zanella et al. | |
| 2010/0016257 | A1 * | 1/2010 | Brown et al. .................. | 514/54 |
| 2010/0215731 | A1 | 8/2010 | Emans et al. | |

FOREIGN PATENT DOCUMENTS

| | | |
|---|---|---|
| WO | WO 01/03750 A1 | 1/2001 |
| WO | WO 03/000056 A1 | 1/2003 |
| WO | WO 03/011345 A1 | 5/2003 |
| WO | WO 03/041724 A1 | 5/2003 |
| WO | WO 2005/112960 A1 | 12/2005 |
| WO | WO 2006/039704 A2 | 4/2006 |
| WO | WO 2007/054939 A2 | 5/2007 |
| WO | WO 2008/065393 A1 | 6/2008 |
| WO | WO 2008/082563 A2 | 7/2008 |
| WO | WO 2010/033137 A1 | 3/2010 |
| WO | WO 2011/014432 A1 | 2/2011 |
| WO | WO 2011014432 A1 * | 2/2011 ............ A61L 27/26 |

OTHER PUBLICATIONS

PCT International Search Report and Written Opinion dated Aug. 21, 2012 issued in PCT/US2012/040675 having common priority (7 pages).
Purac, Purasorb® Brochures, 14 pages (earliest publication date unknown).
Evonik and Bohringer Ingelheim, Resomer® Brochures (earliest publication date unknown).
Supplementary European Search Report and Examiner Comments for European Patent Application No. 12792303.5, dated Jun. 25, 2015, 6 pages.
Gerwin N et al., "Intraarticular drug delivery in osteoarthritis", *Advanced Drug Delivery Reviews*, vol. 58, No. 2, pp. 226-242 (2006).
V.R. Sinha et al., "Poly-[epsilon]-caprolactone microspheres and nanospheres: an overview", *International Journal Pharmaceutics*, vol. 278, No. 1, pp. 1-23 (2004).
R.T. Liggins et al., "Intra0articular treatment of arthritis with microsphere formulations of paclitaxel: biocompatibility and efficacy determinations in rabbits", *Inflammation Research*, vol. 53, No. 8 (2004).
Venkatachalam Natarajan et al., "Formulation and evaluation of quercetin polycaprolactone microspheres for the treatment of rheumatoid arthritis", *Journal Pharmaceutical Sciences*, vol. 100, No. 1, pp. 195-205 (2010).

* cited by examiner

*Primary Examiner* — Johann R Richter
*Assistant Examiner* — Courtney Brown
(74) *Attorney, Agent, or Firm* — Flaster/Greenberg, P.C.

(57) ABSTRACT

Articles for increasing lubrication of a joint are described herein. The articles include resorbable, biocompatible particles having a glass transition temperature within a joint of less than about 37° C. and capable of increasing fluid movement within the joint compared to synovial fluid, viscosupplemental fluid, or combinations thereof. A composition for increasing lubrication of a joint is also disclosed. The composition includes the resorbable, biocompatible particles and a carrier fluid. Methods of lubricating a joint and treating disease affecting the joint such as osteoarthritis are also described herein. The methods include introducing the resorbable, biocompatible particles into a joint.

18 Claims, No Drawings

METHOD, COMPOSITION, AND ARTICLES FOR IMPROVING JOINT LUBRICATION

CROSS-REFERENCE TO RELATED APPLICATION

This application claims the benefit under 35 U.S.C. §119(e) to U.S. Provisional Patent Application No. 61/493,124, filed Jun. 3, 2011, the entire disclosure of which is incorporated herein by reference.

BACKGROUND OF THE INVENTION

1. Field of the Invention

The present invention is directed to assisting in lubricating the joints of mammals and methods of treating osteoarthritis and joint-related pain and ailments.

2. Description of Related Art

Synovial joints such as hip, knee, shoulder and ankle joints are surrounded by an envelope or synovial capsule. The inner layer of the synovial capsule is called a synovial membrane which produces synovial fluid. The fluid is partially stored within the joint cartilage and the remaining fluid circulates freely within the synovial capsule. The capsule maintains the fluid within the joint. In a hip joint, a ring of soft tissue called the acetabular labrum aids in maintaining the fluid in the femoral-acetabular interface. The fluid lubricates and thus reduces friction inside of the joint. In ball and socket synovial joints, the fluid lubricates the ball and socket interface, particularly during movement. For example, the wringing action of the synovial capsule in a hip joint, particularly during flexion and extension movement of the joint, and the paddling action of the femoral neck combine to pump synovial fluid into and across the femoral-acetabular interface thus lubricating the joint. The synovial fluid also cushions the joints during movement, provides oxygen and nutrients to the joint cartilage and removes carbon dioxide and metabolic waste.

Synovial fluid is generally composed of hyaluronic acid, lubricin, proteinases, and collagenases. The hyaluronic acid imparts anti-inflammatory and pain-reducing properties to the normal synovial fluid and contributes to joint lubrication and cushioning during movement. Synovial fluid also exhibits non-Newtonian flow characteristics and thixotropy where the fluid viscosity decreases over time under stress due to movement.

A lack of synovial fluid within the joint, particularly within the ball and socket interface, can aggravate arthritic conditions. Osteoarthritis, the wear and tear of aging, and other injuries or ailments can cause irregularity of the joint surface. In a hip joint, osteoarthritis can also cause fraying of the acetabular labrum resulting in the loss of its gasket-like sealing property. The fraying of the labrum allows migration of the synovial fluid away from the femoral-acetabular interface. Gravity also acts on vertical synovial joints such as hip joints by drawing the synovial fluid downward and away from the femoral-acetabular interface. Moreover, the stress and/or inflammation in synovial joints over time reduce the viscosity of the fluid making it a less effective lubricant and more difficult for the fluid to effectively coat the joint interface. This reduction in synovial fluid flow in the joint interface often results in further reduction in the sealing capacity of the labrum and roughening or incongruity of the joint interface causing increased pain and stiffness in the joint. The pain and stiffness causes a decrease in the motion of the joint resulting in a loss of the pumping action and decrease in the flow of the synovial fluid in the joint interface. This can eventually lead to joint replacement surgery.

To address this problem, artificial lubricants have been developed to replace and/or supplement the lubricating and cushioning action of the synovial fluid in the joint. These lubricants are generally referred to as viscosupplements and generally include hyaluronic acid. However, the degradation of the acetabular labrum associated with osteoarthritis can result in leakage and decreased flow of the viscosupplements. Thus, multiple viscosupplement treatments can be required.

Others have proposed the injection of biodegradable microparticles containing therapeutic agents into the arthritic joints. U.S. Patent Application Publication Nos. 2007/0141160 and 2010/0016257 to Brown, et al. disclose a method of treatment that includes intra-articular injection of biodegradable, polymer microparticles in a carrier vehicle. The microparticles are 5 to 150 microns and may be introduced with a carrier vehicle such as one including a therapeutic agent, for example, hyaluronic acid. The composition is injected into the intra-articular space of a joint to treat joint pain associated with osteoarthritis.

Other treatments to address this issue include joint replacement surgery, arthroscopic surgery, medication and physical therapy. Joint replacement surgery includes replacement of the joint with a prosthetic implant. The prosthetic implant may be constructed of various materials including metal and polymer materials. In addition the typical health risks associated with major joint surgery in older patients, risks and complications of the procedure include infection, dislocation, loosening, or impingement of the implant. In hip replacement surgery, the risks also include fractures of the femur. Moreover, the implant may wear over time causing dissemination of metal and polymer debris within the joint and body, in general.

There exists a need in the art for other innovative methods to improve joint lubrication and thus address the degradation and reduction in the circulation of synovial fluid associated with aging, osteoarthritis, injuries and other ailments. The method will preferably relieve pain and extend joint life to avoid the drawbacks associated with joint replacement surgery and to improve on existing treatments.

BRIEF SUMMARY OF THE INVENTION

The present invention includes articles for increasing lubrication of a joint. The articles are resorbable, biocompatible particles having a glass transition temperature ($T_g$) within the joint of less than about 37° C. and capable of increasing fluid movement within the joint compared to synovial fluid, viscosupplemental fluid, or combinations thereof. The particles preferably have an average particle size of about 0.5 millimeters to about 5 millimeters. The average particle size is most preferably about 3 millimeters.

In a preferred embodiment, the particles have a Young's Modulus of about 10 megapascals to about 500 megapascals, a Poisson's ratio of about 0.1 to about 0.5, and an average density greater than the average density of the fluid within the joint. In a more preferred embodiment, the particles have a Young's Modulus of about 10 megapascals to 100 megapascals. In the most preferred embodiment, the particles have a Young's Modulus of about 10 to about 30 megapascals, a Poisson's ratio of about 0.3, and an average density of about 1.2 g/ml.

In yet another preferred embodiment, the particles resorb in vivo in about 3 to about 18 months. The particles more preferably resorb in vivo in about 12 to about 18 months.

The particles preferably are formed of polymers and copolymers of lactic acid and caprolactone. The particles are more preferably formed of poly(L-lactide-co-caprolactone)

wherein the monomer ratio of L-lactide to caprolactone ranges from about 70:30 to about 5:95. The inherent viscosity of the particles is also preferably about 0.15 to about 3.0 deciliters per gram. Moreover, the particles are preferably spherical.

A composition for increasing lubrication of a joint that includes resorbable, biocompatible particles having a $T_g$ within a joint of less than about 37° C. and capable of increasing fluid movement within the joint compared to synovial fluid, viscosupplemental fluid, or combinations thereof and a carrier fluid is also disclosed herein. The carrier fluid preferably includes synovial fluid, viscosupplemental fluid, and combinations thereof. The composition may also include at least one therapeutic agent such as hyaluronic acid, modified hyaluronic acid, anti-inflammatory medication such as steroids, non-steroidal anti-inflammatory agents, and numbing agents such as lidocaine.

The present invention further includes a method of lubricating a joint that includes introducing particles into a joint, wherein the particles are capable of increasing fluid movement within the joint compared to synovial fluid, viscosupplemental fluid, or combinations thereof and are formed of a resorbable, biocompatible material having a $T_g$ within the joint of less than about 37° C. The particles are preferably introduced into the joint with a cannula. The inside diameter of the cannula is preferably about 2 millimeters to about 6 millimeters and more preferably about 4 millimeters to about 6 millimeters. The particles are also preferably introduced into the joint by arthroscopic visualization, x-ray-guided insertion, radiographically-guided insertion, sonographically-guided insertion or combinations thereof.

The method described above is preferably applied to synovial joints such as a hip, a knee, a shoulder, an ankle, an elbow, a wrist, a toe, a finger, and a spinal facet joint. The method may also be applied to a prosthetic implant or an arthritic joint or otherwise damaged joint.

The present invention further includes a method for treating a disease such as osteoarthritis that causes irregularity of the joint surfaces or breakdown of the soft tissue in the joint by introducing particles into a diseased joint, wherein the particles are capable of increasing fluid movement within the joint compared to synovial fluid, viscosupplemental fluid, or combinations thereof and are formed of a resorbable, biocompatible material having a $T_g$ within the joint of less than about 37° C.

DETAILED DESCRIPTION OF THE INVENTION

The resorbable, biodegradable particles of the present invention increase the lubrication within a joint when introduced into the intra-articular space of the joint compared to synovial fluid, viscosupplemental fluid, or combinations thereof. The increase in fluid movement results in improved lubrication of the joint thus providing treatment of osteoarthritis and improved lubrication of prosthetic implants.

The particles of the present invention are constructed from materials that preferably have a $T_g$ within the joint of less than the normal body temperature of about 37° C. so that the particles are soft enough to prevent impingement within the joint interface. The fluid within the joint may have a plasticizing effect on the particles and thus reduce their $T_g$ in-vivo. Accordingly, particles with a $T_g$ outside of the body greater than 37° C. may still be suitable for the present invention.

The particles are sized so that they can effectively increase the fluid movement within the joint while limiting impingement in the joint interface. The average particle size of the present invention is preferably about 0.5 millimeters to about 5 millimeters. The average particle size is most preferably about 3 millimeters. The particles are preferably uniformly sized. However, significant particle size variations are also acceptable. The particle size may vary depending on the size of the device used to introduce the particles into the joint, the mass required to increase fluid motion within the joint, and volume of the joint space.

The physical parameters that affect the ability of the particles to increase fluid movement within a joint include, but are not limited to, Young's Modulus, Poisson's ratio, and average density. The Young's Modulus of the particles is the ratio of the stress, which has units of pressure, to strain, which is dimensionless. The Young's Modulus of the particles is preferably about 10 to about 500 megapascals. The Young's Modulus is more preferably about 10 to about 100 megapascals and most preferably about 10 to about 30 megapascals.

The Poisson's ratio of the particles is another parameter that affects the ability of the particles to increase the fluid movement within a joint. Poisson's ratio is the ratio, when a sample is stretched, of the contraction or transverse strain (perpendicular to the applied load), to the extension or axial strain (in the direction of the applied load). As shown in Examples 1 and 2 described below, the preferable Poisson's ratio of the particles is about 0.1 to about 0.5. The Poisson's ratio is most preferably about 0.3.

The average density of the particles also contributes to the effectiveness of the particles in increasing fluid movement within the joint. The average density is preferably greater than the density of the fluid within the joint to reduce impingement in the joint interface. An average particle density greater that the density of the joint fluid also allows the particles to be positioned below the level of the joint fluid and thus "push" the fluid across the joint interface during joint motion. For example, the wringing action of the synovial capsule and upward stirring effect of the elliptically-shaped femoral neck facilitates this "pushing" action in a hip joint. The density of synovial fluid is typically about 1.015 g/ml. Accordingly, the average density of the particles is preferably greater than about 1.015 g/ml. The maximum density of the particles is preferably about 2.5 g/ml. The average density is most preferably about 1.2 g/ml.

The particles of the present invention are formed of resorbable, biocompatible materials that are preferably commercially available and FDA-approved for use in the body of a mammal. As used herein, a resorbable material is defined as a material readily degraded in the body and subsequently disposed of by the body or absorbed into the body tissue. As used herein, a biocompatible material is one that is not toxic to the body and does not cause tissue inflammation. The particles of the present invention preferably resorb within the joint in about 3 to about 12 months. The particles most preferably resorb in about 3 to about 6 months. As used herein, "mammal" encompasses humans and animals.

The resorbable, biocompatible particles of the present invention may be formed of natural or synthetic materials. The natural materials may include, among other materials, cat gut, cellulose, chitosan, carrageenan, starch, alginate, hyaluronic acid, and chitin. The synthetic materials preferably include polymers and copolymers. Non-limiting examples of resorbable, biocompatible polymers suitable for making the particles of the present invention may include poly(alpha-hydroxy acid) polymers such as poly(glycolic acid) (PGA), copolymers of lactic acid and glycolic acid (PLGA), polyoxalates, polycaprolactone (PCL), copolymers of caprolactone and lactic acid (PCLA), poly(ether ester) multiblock copolymers based on polyethylene glycol and poly(butylene terephthalate), tyrosine-derived polycarbonates, poly(hydroxybutyrate), poly(alkylcarbonate), poly(orthoesters), polyesters, poly(hydroxyvaleric acid), poly(malic acid), poly(tartaric acid), poly(acrylamides), polyanhydrides, and polyphosphazenes. The copolymers may be random, alternating, block, or graft copolymers. Suitable polymeric materials also include waxes such as glycerol mono- and distearate and the blends thereof. Such polymers may also be combined into blends, alloys or copolymerized with one another. Functional groups for specific properties (e.g., pH adjustment) may be provided. Examples include, but are not limited to, alkyl, aryl, fluoro, chloro, bromo, iodo, hydroxyl, carbonyl, aldehyde, haloformyl, carbonate ester, carboxylate, carboxyl, ether, ester, hydroperoxy, peroxy, caroxamide, amine, ketimine, aldimine, imide, azide, diimide, cyanate, isocyanate, nitrate, nitrile, nitrosooxy, nitro, nitroso, pydridyl, sulfonyl, sulfo, sulfinyl, sulfino, sulfhydryl, thiocyanate, disulfide, phosphino, phosphono, phosphate groups, and combinations thereof. The preferred functional groups include carboxyl, alkyl ester, alkyl ether and hydroxyl groups. The more preferred functional groups include carboxyl and alkyl ester groups.

The preferred particle materials are copolymers of lactic acid and caprolactone. The most preferred material being a copolymer of L-lactide and caprolactone such as poly(L-lactide-co-caprolactone) with an L-lactide to caprolactone monomer ratio of 70:30 or less. Suitable material is commercially available as PURASORB® PLC-7015 from Purac Biomaterials of Gorinchem, The Netherlands.

The inherent viscosity of the polymers and copolymers, measured in deciliters per gram, is a measure of the capability of the polymers and copolymers in solution to enhance the viscosity of the solution. The inherent viscosity is dependent upon the length of the polymer and copolymer chains and increases with increasing polymer or copolymer molecular weight. The inherent viscosity of the polymers or copolymers forming the particles is preferably about 0.15 deciliters per gram to about 3.0 deciliters per gram.

The particles may be formed of any shape including, but not limited to spherical, oval, elliptical, cuboidal, pyramidal, or cruciform. However, the particles are preferably spherical to minimize impingement in the joint interface.

The particles also may be formed of any known method for forming particles of the material and size described above. The particles are preferably formed via a melt-processing technique such as injection molding. Injection molding is a manufacturing process for producing articles from polymeric materials. The process includes first feeding the polymeric raw material into a container for heating. The resultant heated material is then mixed and added to a mold where it cools to form the particles of the present invention. Other acceptable techniques for producing the particles of the present invention include other solvent based processes such as double emulsion/solvent evaporation and spray drying, extrusion, and cryoformation.

The present invention further includes a composition for increasing lubrication of a joint. The composition includes the particles described above and a carrier fluid. The carrier fluid may include, but is not limited to, aqueous solutions including physiologic electrolyte or ionic solutions such as saline solution or lactated ringer's solution, chondroitin sulfate, synovial fluid, viscosupplemental fluid such as hyaluronic acid commercially available as ORTHOVISC® produced by DePuy Ortho Biotech Products of Raritan, N.J., and combinations thereof. The composition may also include at least one therapeutic agent for treating osteoarthritis or other disease affecting the joints. The therapeutic agent may include hyaluronic acid, modified hyaluronic acid, anti-inflammatory medication such as steroids, non-steroidal anti-inflammatory agents, numbing agents such as lidocaine or the like.

The present invention further includes a method for lubricating a joint by introducing the particles described above into the joint. The particles may be introduced into the joint using any suitable device such as through a catheter, infusion pump, needle or a cannula. The particles are preferably introduced into the joint using a cannula with an inside diameter of about 2 millimeters to about 6 millimeters and more preferably about 4 millimeters to about 6 millimeters. The particles are preferably introduced into the joint by direct arthroscopic visualization, x-ray guided insertion, radiographically-guided insertion, sonographically-guided insertion or combinations thereof, although other known methods may also be used.

The number of particles introduced into the joint is dependent on the average size of the particles and the type of joint. The number of particles introduced into the joint is preferably an effective amount to increase fluid movement within the joint. In a typical hip joint, the volume of the synovial capsule is about 20 ml to about 200 ml. For an average particle size of about 3 millimeters, the number of particles introduced into the joint may include, but is not limited to, about 5 to about 1,000 particles. The number of particles is more preferably about 5 to about 100 particles.

The method may be used to lubricate any type of joint. However, the joint is preferably a synovial joint such as a hip, a knee, a shoulder, an ankle, an elbow, a wrist, a toe, a finger, and/or a spinal facet joint. The joint is more preferably a hip, ankle or knee joint. The method can also be used for lubricating a prosthetic implant or an arthritic or other diseased or injured joint. The method may further include introducing the particles in a carrier fluid including, but not limited to, aqueous solutions including physiologic electrolyte or ionic solutions such as saline solution or lactated ringer's solution, chondroitin sulfate, synovial fluid, viscosupplemental fluid, and combinations thereof and/or a therapeutic agent such as hyaluronic acid, modified hyaluronic acid, anti-inflammatory medication such as steroids, non-steroidal anti-inflammatory agents, numbing agents such as lidocaine or the like.

A method for treating a disease that causes irregularity of the joint surfaces or breakdown of the soft tissue in the joint such as osteoarthritis is also disclosed herein. The method includes introducing the particles described above into an arthritic joint, wherein the particles are capable of increasing fluid movement within the joint compared to synovial fluid, viscosupplemental fluid, or combinations thereof. The increase in fluid movement within the joint alleviates symptoms associated with osteoarthritis including pain and stiffness. Further, the use of the particles may forestall or eliminate the need for joint replacement surgery. The invention will now be illustrated in accordance with the following non-limiting examples.

EXAMPLES

Example 1 illustrates the effectiveness of polymer particles in lubricating a joint compared with joint fluid alone. Example 2 evaluates polymers and copolymers to determine their suitability for forming the particles of the present invention.

Example 1

A simulation was run on a three-dimensional model of a hip joint to evaluate the effectiveness of polymer particles in lubricating a joint compared with joint fluid alone. The model assumed the femur and the concave surface of the pelvis known as the acetabulum are rigid, the synovial capsule and particles are elastic, and the synovial fluid has similar properties to water. The capsule, fluid, and particle physical parameters are summarized in Table 1.

TABLE 1

| Material | Density (g/ml) | Young's Modulus (MPa) | Poisson's Ratio (dimensionless) |
|---|---|---|---|
| Capsule | 1.5 | 50 | 0.1 |
| Fluid | 1.0 | — | — |
| Particles | 1.5 | 2,360 | 0.3 |

Two simulations were run using Smooth Particle Hydrodynamics to evaluate the effectiveness of the particles in increasing the fluid movement and thus lubrication of a hip joint. The first simulation includes fluid particles only and assumes the fluid particles are located in the space between the synovial capsule and the neck of the femur and the space between the acetabulum and the femoral head. The second simulation includes fluid particles mixed with 3-mm diameter polymer particles. Prior to the simulation, the synovial capsule was shrunk by lowering its temperature to simulate pretension of the joint. The femur was then flexed forward 35 degrees, extended 60 degrees and finally returned to its original position. The kinetic energy and the number of fluid particles located between the femoral head and acetabulum were modeled at multiple times during the simulation. The results are shown in Table 2.

TABLE 2

| | Number of Fluid Particles Between Femoral Head and Acetabulum[1] | | Kinetic Energy of Fluid Particles Between Femoral Head and Acetabulum (N mm) | |
|---|---|---|---|---|
| Time (sec) | Without Polymer Particles | With Polymer Particles | Without Polymer Particles | With Polymer Particles |
| 0.000 | 1113 | 1113 | 0 | 0 |
| 0.040 | 2473 | 2394 | 0.128 | 0.224 |
| 0.0585 | 2527 | 2409 | 0.108 | 0.219 |
| 0.091 | 2573 | 2467 | 0.114 | 2.283 |
| 0.092 | 2560 | 2446 | 0.087 | 0.879 |

[1]The total number of fluid particles in the capsule remained constant at 7,034 during the simulation. Fifty-one (51) polymer particles were added to the capsule for the second simulation.

The movement of the fluid particles was also monitored during the simulations. The fluid particles traveled longer distances within the joint when mixed with the polymer particles compared to the fluid particles alone.

Based on the simulations, addition of the polymer particles caused up to a 20-fold increase in the kinetic energy of the fluid particles within the hip joint. Further, the polymer particles increased the distance each fluid particle traveled while the hip was in motion. Accordingly, this Example demonstrates that the polymer particles can increase fluid movement in the joint, thereby, increasing lubrication of the joint.

Example 2

Several FDA-approved, biocompatible, resorbable polymers and copolymers were tested to identify the preferred materials for forming the particles of the present invention. Various physical parameters of the polymers and copolymers were tested to evaluate suitability for forming the particles of the present invention. Table 3 identifies the materials.

TABLE 3

| Material | Tradename | Manufacturer | Comments |
|---|---|---|---|
| Poly(L-lactide-co-caprolactone) | PURASORB® PLC-8516 | Purac Biomaterials | 85:15 L-lactide/caprolactone monomer ratio |
| Poly(L-lactide-co-caprolactone) | PURASORB® PLC-7015 | Purac Biomaterials | 70:30 L-lactide/caprolactone monomer ratio |
| Poly(L-lactide-co-caprolactone) | RESOMER® LC-703-S | Boehringer-Ingelheim of Ridgefield, Connecticut | 70:30 L-lactide/caprolactone monomer ratio |
| Poly(D,L-lactide-co-glycolide) | RESOMER® RG-509-S | Boehringer-Ingelheim | 50:50 D,L-lactide/glycolide monomer ratio |
| Polydioxanone | RESOMER® X-206-S | Boehringer-Ingelheim | Homopolymer |
| Poly(D,L-lactide) | RESOMER® R-207-S | Boehringer-Ingelheim | Homopolymer |

The materials were first tested to determine whether the densities of the materials were greater than synovial fluid (i.e., 1.015 g/ml). Granules of each material were placed in a vial of a saline test solution with a density of 1.015 g/ml. All of the materials sank within the solution suggesting a density greater than that of synovial fluid. Accordingly, all the materials had a density greater than that of synovial fluid.

The materials were then tested in a synthetic synovial fluid test solution to simulate the properties of the samples within an osteoarthritic joint. Approximately 40 weight percent ORTHOVISC® was added to the saline test solution to simulate typical synovial fluid within an osteoarthritic joint based on a target viscosity of 1,400 centipoise at 25° C. Granules of each material were then added to a 1.0 ml vial of the synthetic synovial fluid test solution and allowed to equilibrate for three weeks. The samples were then analyzed via Differential Scanning calorimetry (DSC) from −40° C. to 90° C. to determine the $T_g$. The equilibrated $T_g$ based on the DSC results and the melting temperature ($T_m$) and $T_g$ of the dry materials are shown in Table 4.

TABLE 4

| Sample | Dry $T_m$ (° C.) | Dry $T_g$ (° C.) | Equilibrated $T_g$ (° C.) |
|---|---|---|---|
| RESOMER® R-207-S | — | 50-60 | 47 |
| RESOMER® LC-703-S | 108-111 | 20 | * |
| RESOMER® RG-509-S | — | 40-50 | 36 |
| RESOMER® X-206-S | 110 | −16 | * |
| PURASORB® PLC-7015 | 108-111 | 20 | 9 |
| PURASORB® PLC-8516 | 130 | 40 | 28 |

*: The RESOMER® LC-703-S and RESOMER® X-206-S yielded no clear $T_g$ over the DSC temperature range.

The samples with an equilibrated $T_g$ lower than body temperature of 37° C. based on DSC results were then qualitatively tested for stiffness. The previously equilibrated samples with $T_g$ lower than 37° C., RESOMER® RG-509-S, PURASOR® PLC-7015 and PURSORB® PLC-8516, were heated to 37° C. for 24 hours. The samples were then examined with a spatula to qualitatively evaluate the stiffness of the materials. The PURASORB® PLC-7015 was elastic after heating while the other two materials were inflexible and likely unsuitable due to potential impingement in the joint after implantation. The physical properties of the PURASORB® PLC-7015 are reproduced in Table 5.

TABLE 5

| Sample | Density (g/ml) | Young's Modulus (MPa) | Poisson's Ratio |
|---|---|---|---|
| PURASORB® PLC-7015 | 1.22 | 30 | 0.3 |

As illustrated in these Examples, the present invention fulfills a need in the art for an innovative method to improve joint lubrication and thus address the degradation and reduction of synovial fluid associated with aging, osteoarthritis, injuries and other ailments.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A method of lubricating a joint comprising introducing particles into a joint, wherein the particles are capable of increasing fluid movement within the joint compared to synovial fluid, viscosupplemental fluid, or combinations thereof and are formed of a resorbable, biocompatible material, wherein an average particle size is about 0.5 mm to about 5 mm.

2. The method according to claim 1, further comprising introducing the particles into the joint through a cannula.

3. The method according to claim 2, wherein an inside diameter of the cannula is about 2 millimeters to about 6 millimeters.

4. The method according to claim 2, wherein an inside diameter of the cannula is about 4 millimeters to about 6 millimeters.

5. The method according to claim 3, further comprising introducing the particles into the joint by arthroscopic visualization, x-ray-guided insertion, radiographically-guided insertion, sonographically-guided insertion or combinations thereof.

6. The method according to claim 1, wherein the joint is a synovial joint.

7. The method according to claim 6, wherein the synovial joint is selected from the group consisting of a hip, a knee, a shoulder, an ankle, an elbow, a wrist, a toe, a finger, and a spinal facet joint.

8. The method according to claim 1, wherein the joint is a prosthetic implant.

9. The method according to claim 1, wherein the joint is an arthritic joint.

10. The method according to claim 1, wherein the average particle size is about 3 millimeters.

11. The method according to claim 1, further comprising introducing the particles into the joint with a carrier fluid and/or a therapeutic agent.

12. The method according to claim 11, wherein the carrier fluid comprises saline solution, lactated ringer's solution, chondroitin sulfate, synovial fluid, viscosupplemental fluid, and combinations thereof.

13. A method for treating a disease that causes irregularity of the joint surfaces or breakdown of the soft tissue in the joint comprising introducing particles into a diseased joint, wherein the particles are capable of increasing fluid movement within the joint compared to synovial fluid, viscosupplemental fluid, or combinations thereof and are formed of a resorbable, biocompatible material, wherein an average particle size is about 0.5 mm to about 5 mm.

14. The method according to claim 13, wherein the disease is osteoarthritis.

15. A method of lubricating a joint comprising introducing particles into a joint, wherein the particles are capable of increasing fluid movement within the joint compared to synovial fluid, viscosupplemental fluid, or combinations thereof and are formed of a resorbable, biocompatible material, wherein an average density of the particles is about 1.015 g/ml to about 2.5 g/ml.

16. The method according to claim 15, wherein an average particle size is about 0.5 mm to about 5 mm.

17. A method for treating a disease that causes irregularity of the joint surfaces or breakdown of the soft tissue in the joint comprising introducing particles into a diseased joint, wherein the particles are capable of increasing fluid movement within the joint compared to synovial fluid, viscosupplemental fluid, or combinations thereof and are formed of a resorbable, biocompatible material, wherein an average density of the particles is about 1.015 g/ml to about 2.5 g/ml.

18. The method according to claim 17, wherein an average particle size is about 0.5 mm to about 5 mm.

* * * * *